United States Patent [19]

Shinohara

[11] Patent Number: 5,298,424
[45] Date of Patent: Mar. 29, 1994

[54] AUTOMATIC CHEMICAL ANALYSIS SYSTEM AND AUTOMATIC CHEMICAL ANALYSIS METHOD

[75] Inventor: Hiroo Shinohara, Tochigi, Japan

[73] Assignee: Kabushiki Kaisha Toshiba, Kawasaki, Japan

[21] Appl. No.: 858,082

[22] Filed: Mar. 26, 1992

[30] Foreign Application Priority Data

Mar. 26, 1991 [JP] Japan .................................. 3-61669

[51] Int. Cl.$^5$ .............................................. G01N 35/00
[52] U.S. Cl. ........................................ 436/43; 422/63;
422/67; 422/100; 436/179; 436/180
[58] Field of Search ...................... 422/63, 67, 100;
436/43, 179, 180

[56] References Cited

U.S. PATENT DOCUMENTS

| | | | |
|---|---|---|---|
| 4,130,394 | 12/1978 | Negersmith | 422/58 |
| 4,591,568 | 5/1986 | Banno et al. | 436/180 |
| 5,061,639 | 10/1991 | Lung et al. | 422/100 X |

FOREIGN PATENT DOCUMENTS 0255026  2/1988  European Pat. Off.

OTHER PUBLICATIONS

Patent Abstracts of Japan, vol. 015, No. 363 (P-1251), Sep. 12, 1991, & JP-A-31 40 844, Jun. 14, 1991, Nakano Kiyokazu, "Multi-Item Analysis of Minute Sample".

*Primary Examiner*—Jill A. Johnston
*Attorney, Agent, or Firm*—Oblon, Spivak, McClelland, Maier & Neustadt

[57] ABSTRACT

A chemical analysis system including a suction unit for sucking an amount of a sample from a sample vessel and determining whether or not the sucked sample is of a sufficient amount for analysis. If the sucked amount is of a sufficient amount, it is transferred directly to a reaction vessel for mixture with a reagent in a measurement unit for analysis. If the sucked amount is of an insufficient amount, it is initially transferred to a temporary sample storage unit in order to detect the amount of insufficiency and then is transferred to the measurement unit for mixture with the reagent and also with a dilution solution which is added to the insufficient sample in an amount determined by the amount of insufficiency determined in the temporary sample storage unit. Then, the analysis of the previously insufficient amount of sample is performed taking into account the amount of dilution solution added to the previously insufficient amount of sample. A control unit is providing for controlling the overall operation of the system.

7 Claims, 4 Drawing Sheets

AUTOMATIC CHEMICAL ANALYSIS SYSTEM AND AUTOMATIC CHEMICAL ANALYSIS METHOD

BACKGROUND OF THE INVENTION

The present invention relates to an automatic chemical analysis system particularly for detecting a fact as to whether or not a necessary amount of a sample is sucked and an automatic chemical analysis method utilizing the system.

There is known an automatic chemical analysis system which uses, for example, blood serum taken from a human body as a sample and causes the sample to react with a desired reagent according to an analysis item. A specific component of the thus prepared reacted solution is then analyzed.

In order to perform this analysis, first, a necessary amount of a sample to be analyzed is sucked from a sample vessel by a sample suction probe, supplied to a reaction vessel disposed on a measurement line and then reacted with a reagent supplied to the same reaction vessel almost at the same time with the supply of the sample. The resulting reaction solution is thereafter measured by using, for example, a colorimetric method to thereby analyze the concentration of the above specific component. The result of the analysis for each analysis item is outputted and reported by being displayed to a monitor or printed by a printer.

When the sample is sucked by the sample suction probe as described above, a monitor unit is provided for detecting whether or not the sample having an amount necessary for analysis is in fact sucked, and if the amount of the sample necessary for the analysis is not sucked, an occurrence of an insufficient suction error is reported as a result of the analysis.

Incidentally, the conventional automatic chemical analysis system has a problem in that when an amount necessary for analysis of the sample is not sucked, the sample must be remeasured because the result of the analysis thereof lacks reliability, and additional time is thus consumed and the sample is wasted.

More specifically, the conventional suction monitor unit only reports that an amount of the sample is insufficient. The result of the analysis for an item for which an insufficient suction error is reported is not reliable and this item must be remeasured. Further, in an automatic chemical analysis system of the type in which a multiplicity of analysis items are simultaneously measured by once sucking a sample, an insufficient suction error is reported on the result of all the items unless a quantitative analysis of an insufficient amount is accurately performed. Accordingly, these items have to be remeasured to ensure the accuracy of data.

Nevertheless, since a sample taken from a human body is precious and limited in amount, the use of the sample, which originally has a small content, for remeasurement is wasteful and not desirable. Further, it is sometimes required to take the sample again from a human body, which imposes a burden upon the human body which is unhealthy even if the sample is not taken therefrom.

Further, there is also known an analysis system provided with a dilution function, and it is contemplated to cope with the shortage of the sample by making use of this dilution function, but it is difficult to specify a magnification ratio of dilution.

SUMMARY OF THE INVENTION

An object of the present invention is to substantially eliminate defects or drawbacks encountered in the prior art described above and to provide an automatic chemical analysis system which does not need the remeasurement of a sample even if the sample is sucked in an insufficient amount.

This and other objects of the present invention can be achieved, in one aspect, by providing an automatic chemical analysis system in which a sample and a reagent supplied in a reaction vessel disposed in a measurement line are subjected to analysis treatment and the analyzed result is then reported, comprising a suction means for sucking the sample from a sample vessel, a detecting means for detecting a fact as to whether a sucked amount of the sample is sufficient or insufficient for the analysis, a calculation means for calculating an insufficient amount of the sucked sample when it is detected by the detecting means that an insufficient amount of the sample necessary for the analysis has been sucked and for obtaining information regarding an amount of a dilution solution for compensating for the insufficient amount of the sample, an analyzing means for carrying out an analysis treatment after dilution of the sample in accordance with the information of the amount of the dilution solution and a correction means for compensating for a result of the analysis treatment in accordance with the information of the amount of the dilution solution.

More concretely, there is provided an automatic chemical analysis system comprising, a sample setting unit for accommodating a plurality of sample vessels each in which a sample is contained, a suction unit for sucking the sample in the sample vessel and detecting an amount of the sucked sample, a sample temporary storage unit for storing the sample vessel in which an insufficient amount of the sample is contained, a dilution unit for diluting the sample contained in the sample vessel stored in the sample temporary storage unit, a reagent setting unit for supplying a reagent into the sample vessel, a measurement unit including a sample reaction vessel into which the reagent is additionally supplied from the reagent setting unit and the sample temporary storage unit, a control means for controlling operations of the suction unit, the sample temporary storage unit and the dilution unit, the control means including an element for instructing that a sample vessel containing the sufficient amount of the sample is to be directly transferred to the measurement unit and a sample vessel containing the insufficient amount of the sample is to be transferred to the sample temporary storage unit, an element for calculating an insufficient amount of the sucked sample in the sample vessel transferred to the sample temporary storage unit when it is detected by the detecting element that an amount of the sample necessary for the analysis is not sucked and for obtaining an information regarding an amount of a dilution solution for compensating for the insufficient amount of the sample, an element for carrying out an analysis treatment after dilution of the sample in accordance with the information of the amount of the dilution solution and an element for compensating for a result of the analysis treatment in accordance with the information of the amount of the dilution solution, and a display unit for displaying a result of the analysis of the sample.

In a preferred embodiment, the suction unit includes a sample suction probe for sucking the sample from the sample vessel disposed in the sample setting unit and a suction monitor for detecting the fact as to whether or not a sufficient amount of a sample has been sucked. The sample temporary storage unit includes a sample quantity determination probe for determining an amount of the sample in the sample vessel transferred to the sample temporary storage unit, the sample quantity determination probe being provided with a level sensor for detecting a surface level of the sample contained in the sample vessel. The dilution solution is pure water and the sample of the insufficient amount is diluted by the pure water with a calculated magnification ratio of dilution. The result of the analysis treatment is converted into an actual concentration value by considering the magnification ratio of dilution.

In another aspect of the present invention, there is provided an automatic chemical analysis method for sucking a sample in a sample vessel and analyzing the sample in a measurement line, comprising the steps of:
- sucking a sample from the sample vessel;
- discriminating whether the sucked sample is of a sufficient or insufficient amount;
- transferring a sample discriminated to have a sufficient amount directly to a measurement line and separately transferring a sample discriminated to have an insufficient amount;
- calculating an insufficient amount of the separately transferred sample;
- calculating a magnification ratio for dilution for the sample of the insufficient amount;
- supplying a dilution solution by an amount in accordance with the calculated magnification ratio for dilution;
- transferring the thus diluted sample to the measurement line;
- calculating concentration of the samples transferred to the measurement line;
- calculating an actual concentration with respect to the diluted sample in accordance with the magnification ratio for dilution; and
- carrying out a chemical analysis of the sample.

According to the automatic chemical analysis system described above, when it is detected by the suction monitor means that the amount of the sucked sample is less than the amount necessary for analysis, this sample is transferred to the temporary sample storage unit without being transferred to the measurement unit. Thereafter, the sample is supplied to another vessel, the shape and size of which are preliminarily known, and then the insufficient amount of the sample is calculated on the basis of the known shape and size of the vessel and a magnification ratio for dilution for increasing the amount of the sample to the amount necessary for analysis is determined. Next, the sample is transferred to the measurement unit to be diluted there and subjected to an analyzing process, and thereafter, the result of the analysis is corrected on the basis of the dilution information. With this arrangement, even if a sample the sucked amount of which is detected to be insufficient is used as it is and analyzed after it has been diluted, and thus the sample is not wasted. Furthermore, since a remeasurement is not necessary, time can be saved.

BRIEF DESCRIPTION OF THE DRAWINGS

For a better understanding of the present invention and to show how the same is carried out, reference will be first made, by way of the preferred embodiment, to the accompanying drawings, in which.

DESCRIPTION OF THE PREFERRED EMBODIMENT

An automatic chemical analysis system to which the present invention is applicable generally comprises an analyzing unit and a data processing unit. The analyzing unit includes a sampler, i.e. sample setting unit, generally having a circular configuration and being rotatable, in which a plurality of sample vessels containing samples to be analyzed are set, a sample dilution means for diluting the sample as occasion demands and a measuring unit including a constant temperature container and an agitation means, for example for maintaining constant the temperature of the sample. In such an analysis system, these members are arranged on a table, for example, of the analyzing unit. A reagent supply container in which a reagent is contained is disposed in the vicinity of the sample analyzing unit.

The data processing unit includes an overall control unit as a central processing unit (CPU) provided with a display means or a printer. The data from or to the respective means are controlled by this data processing unit.

A preferred embodiment of the present invention will be described hereunder with reference to FIGS. 1 to 6.

Figure 1:
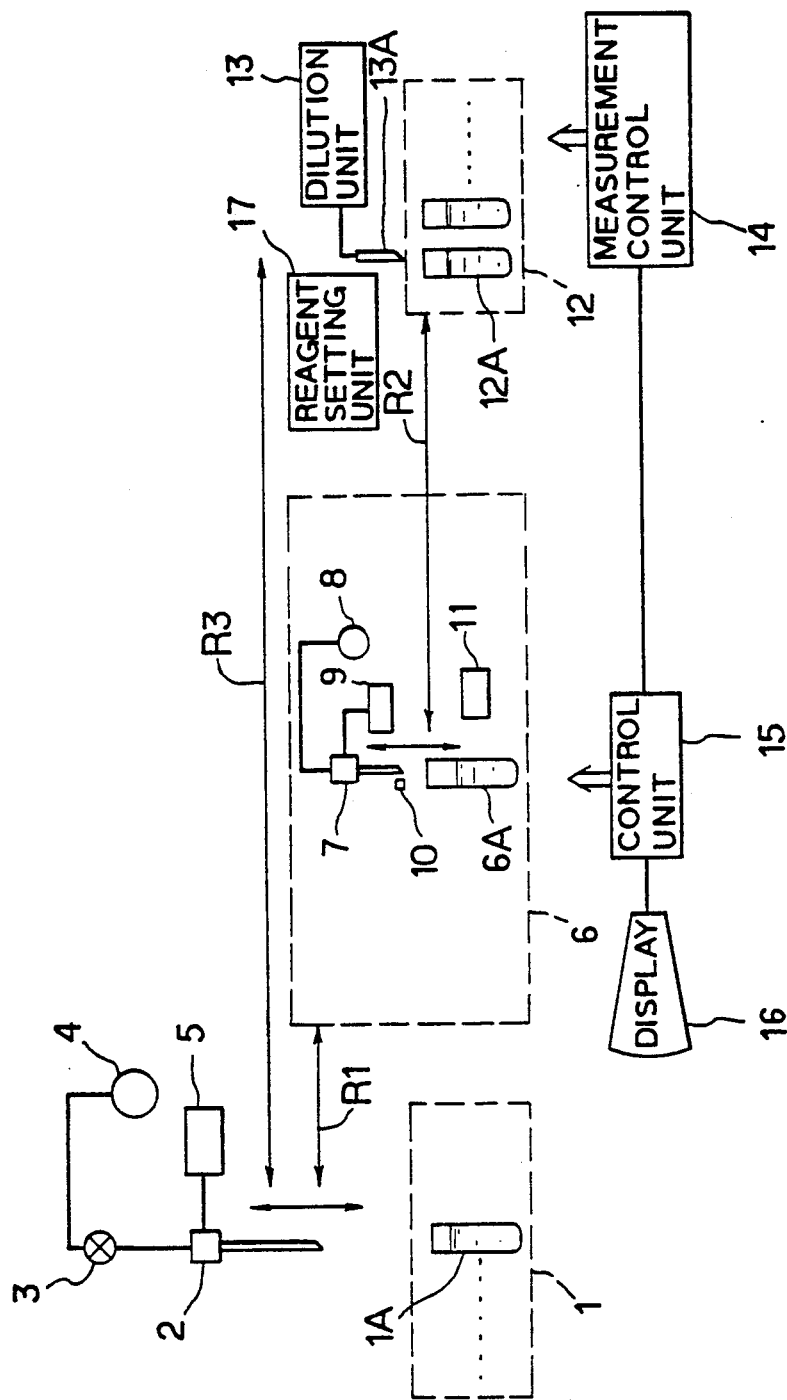
FIG. 1 shows a shematic diagram of an automatic chemical analysis system according to the present invention.

FIG. 1 is a diagram showing an arrangement of one embodiment of an automatic chemical analysis system according to the present invention, wherein a sample setting unit 1 includes a plurality of sample vessels 1A such as test tubes each containing a sample to be analyzed, these sample vessels 1A being sequentially moved. FIG. 1 shows the case in which only one sample vessel 1A is provided. Referring to FIG. 1, a sample suction probe 2 is disposed above the sample vessel 1A and can be vertically and horizontally moved by a drive unit 5. A pump 4 is connected to the sample suction probe 2 through a suction monitor 3 and the probe 2 sucks an amount of a sample necessary for analysis when it is lowered into the sample vessel 1A.

The suction monitor 3 has a function for detecting whether or not a necessary amount of the sample is sucked when the sample is sucked. A result of the detection is supplied to an overall control unit 15 to be described hereinlater and it is determined on the basis of this result whether the sample is to be directly transferred to a direct measurement line 12 such as a route R3 or to be transferred to a temporary sample storage unit 6 such as a route R1.

A sample sucked by the sample suction probe 2 which is of a sufficient amount for analysis is directly transferred to the measurement line 12 in a horizontal direction by being driven by the drive unit 5 and supplied to a reaction vessel 12A prepared in the measurement line 12, whereas the sample the sucked amount of which is not sufficient for analysis is transferred to the temporary sample storage unit 6 instead of being transferred to the measurement line 12.

A reagent setting unit 17 is disposed in the vicinity of the measurement line 12 from which a desired reagent is supplied to the reaction vessel 12A by a reagent gathering unit, not shown, almost at the same time with the supply of the sample. Further, when an indication of the dilution is made, pure water is supplied to the reaction vessel 12A from a dilution unit 13 through a dilution probe 13A. The result of analysis of the sample subjected to an analyzing process at the measurement line 12 under the control of a measurement control unit 14 is supplied to the overall control unit 15 and reported to a display unit 16 composed of a CRT (cathod ray tube) monitor or printer.

The temporary sample storage unit 6 is composed of a sample vessel 6A such as a test tube to which the sample transferred by the sample suction probe 2 is supplied, a sample quantity determination probe 7 which is to be lowered into the vessel 6A by a drive unit 9 for determining the quantity of the sample, a level detection unit 10 for detecting the level of the sample in the vessel 6A, a pump 8 for sucking the sample, a cleaning unit 11 for cleaning the vessel 6A, and the like. The shape and size of the sample vessel 6A to which an insufficient amount of a sample is supplied is previously known. The sample suction probe 2 having transferred a sample to the sample temporary storage unit 6 returns to the original position thereof at once for sucking other sample. Therefore, the operation of the sample suction probe 2 is carried out concurrently with the operation of the sample quantity determination probe 7.

The sample quantity determination probe 7 is lowered into the vessel 6A by the drive unit 9, and when the level detection unit 10 attached to the extreme end of the probe 7 detects the sample level, a detection signal is transmitted to the drive unit 9. With this arrangement, the drive unit 9 calculates an amount (volume) of the sample in the vessel 6A by calculating a moving amount of the probe 7 lowered into the vessel 6A and determining a height of the level of the sample based on the previously known shape and size of the vessel 6A.

Figure 2:
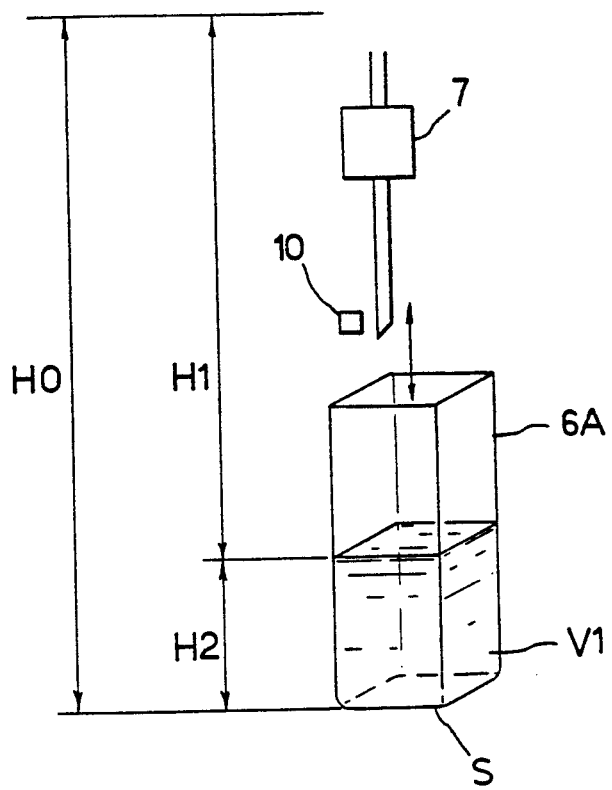
FIG. 2 is an explanatory of a principal embodiment of the present invention.

FIG. 2 describes a method of calculating an amount of the sample as explained above. In FIG. 2, H0, H1, H2, V1 and S are defined as follows.

H0: height from the bottom of the vessel 6A to the initial position of the probe 7
H1: amount of movement of the probe 7 before the sample level is detected
H2: height of the sample in the vessel 6A
V1: volume of the sample
S: bottom area of the vessel 6A
Therefore, V1 is determined as follows.

$$V1 = S \times H2 = S \times (H0 - H1) \qquad (1)$$

An accuracy of the value V1 depends on such conditions as a dimensional accuracy of the sample vessel 6A, an accuracy of the positional relationship between the sample vessel 6A and the sample quantity determination probe 7, an accuracy of movement of the sample quantity determination probe 7, a sensitivity of the level detection unit 10, and the like. According to the present invention, however, when the error thereof is known, the object of the invention can be achieved. The error is now assumed as a value of Ve. Further, although the sample is sucked by the sample quantity determination probe 7, transferred to the measurement line 12 such as the route R2 and supplied to the reaction vessel 12A thereof, it is difficult to entirely suck the amount of the sample corresponding to V1 and thus it cannot be avoided that a slight amount of the sample remains. When this remaining amount is represented by Vd, an amount V2 to be used for measurement will be eventually expressed as follows.

$$V2 = V1 - Ve - Vd \qquad (2)$$

Therefore, the amount V2 is sucked from the vessel 6A by the pump 8 through the sample quantity determination probe 7, transferred to the measurement line 12, and supplied to the reaction vessel 12A. Here, the amount V2 is naturally smaller than the amount V0 necessary for measurement. The insufficient amount $V = (V0 - V2)$ is supplemented with pure water supplied from the dilution unit 13.

More specifically, the sample is diluted by a magnification ratio for dilution D shown by the following formula $$D = (V2 + V)/V2 = V0/V2 \qquad (3)$$

This magnification ratio for dilution D is stored in the measurement control unit 14.

The diluted sample is analyzed in the measurement line 12 in the same way as that of a usual sample for obtaining a measured value. Then, the measured value is multiplied by the magnification ratio for dilution D by means of the above measurement control unit 14 storing the same and converted to an actual concentration value, which is sent to the overall control unit 15 and reported to the display unit 16. It is to be noted that an additional display may be made to indicate that the insufficient amount of the sample has been diluted.

The operation of the present invention will be described hereunder.

Figure 3:
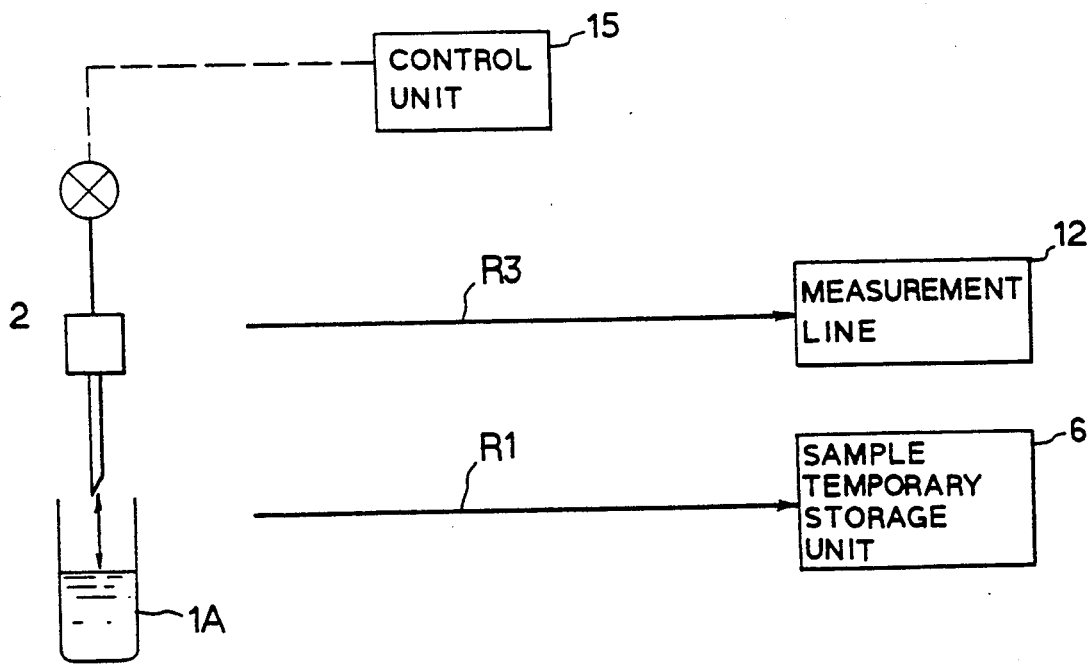
FIG. 3 is an explanatory illustration of a suction unit and associated units of the automatic chemical analysis system of FIG. 1.
Figure 4:
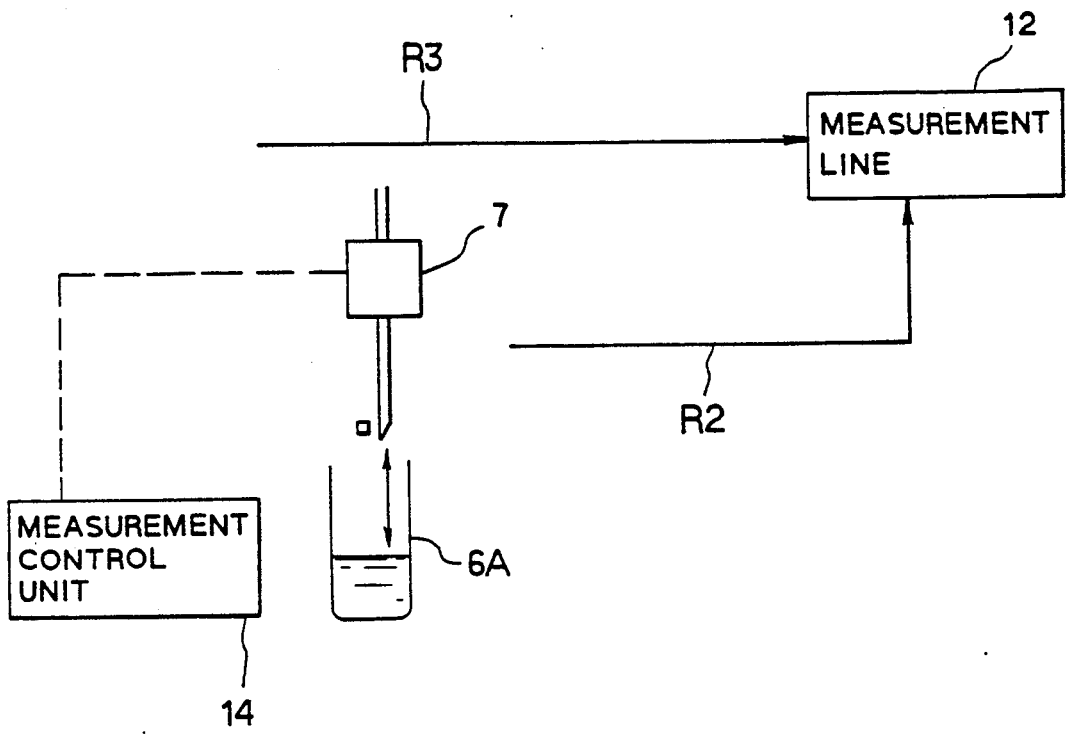
FIG. 4 is an explanatory illustration of a sample temporary storage unit and associated units of the automatic chemical analysis system of FIG. 1.

As shown in FIG. 3, respective samples requested to be analyzed are contained in the sample vessels 1A in the sample setting unit 1 and sucked by the sample suction probe 2 in accordance with analysis items, and the suction monitor 3 detects whether or not each sample has been sucked in an amount necessary for analysis. The sample the sucked amount of which is determined insufficient as the result of the detection is transferred to the temporary sample storage unit 6 by the above sample suction probe 2 through the route R1 and supplied to the sample vessel 6A prepared there, as shown in FIG. 4.

The amount V1 of the insufficiently sucked sample is determined from the formula (1) in the temporary sample storage unit 6 in the manner mentioned above. Further, the amount V2 of the sample capable of being used for measurement is determined on the basis of the formula (2), and furthermore, an insufficient amount is determined from the amount V0 necessary for measurement. In addition, a magnification ratio for dilution D for determining an amount to be added to the amount V2 is calculated on the basis of the formula (3) and stored in the measurement control unit 14.

Figure 5:
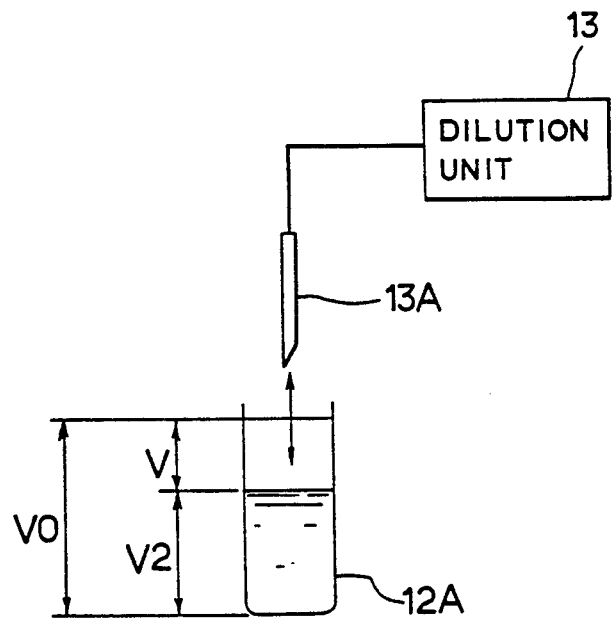
FIG. 5 is an explanatory illustration of a dilution unit of the automatic chemical analysis system of FIG. 1.
Figure 6:
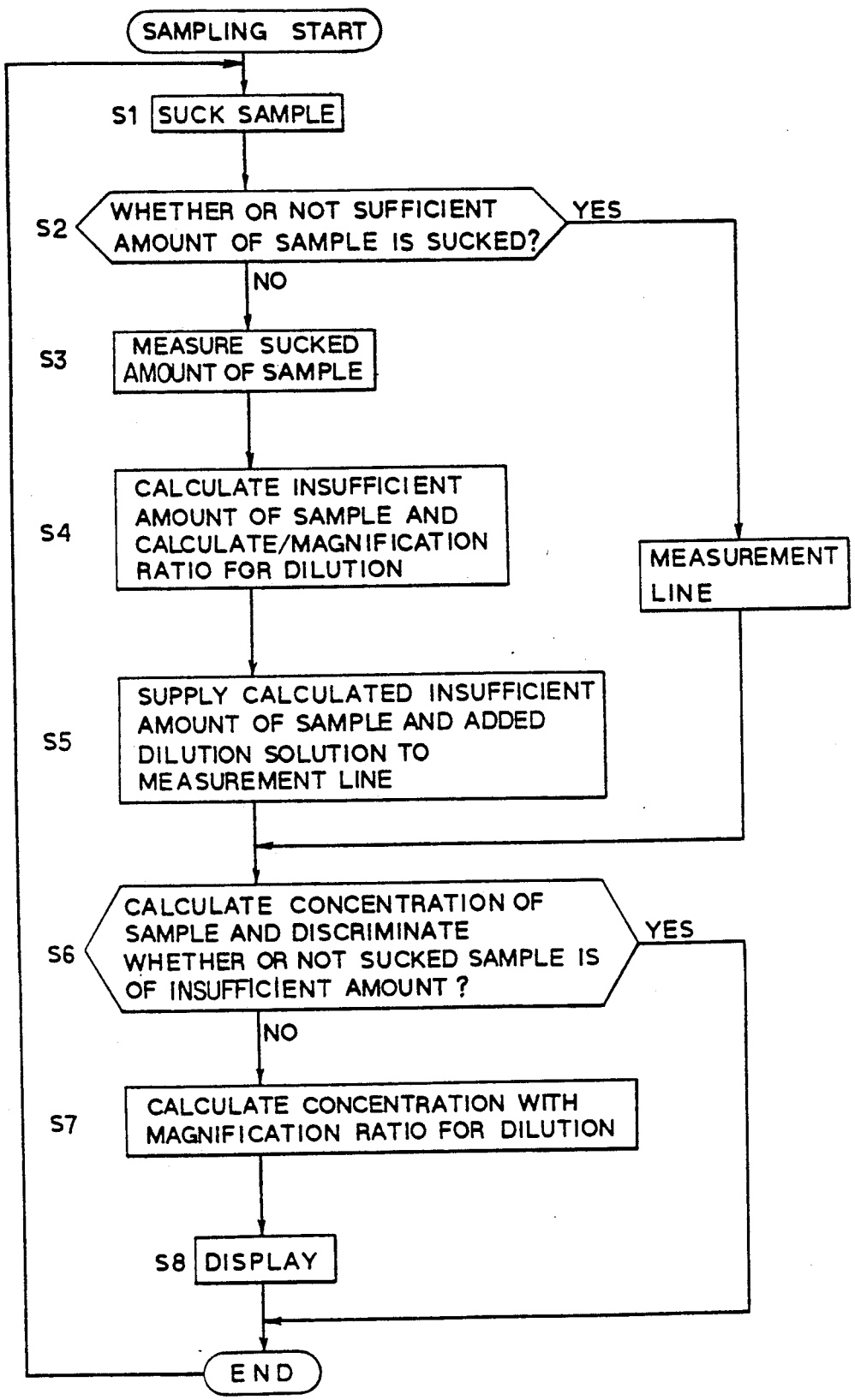
FIG. 6 is an explanatory flowchart of automatic chemical analyzing processes carried out according to the present invention.

Subsequently, this sample is sucked by the sample quantity determination probe 7, transferred to the measurement line 12 through the route R2 and supplied to the reaction vessel 12A. Referring to FIG. 5, pure water of the amount corresponding to the above insufficient amount V is supplied to the sample in the reaction vessel 12A from the dilution unit 13 through the dilution probe 13A under the control of the measurement control unit 14 so that the magnification ratio for dilution D can be obtained. Thereafter, the sample is analyzed by a colorimetric method similarly to a usual sample to obtain a measured value.

Next, the measured value is corrected by being multiplied with the magnification ratio for dilution D by the measurement control unit 14 and converted to an actual concentration value. The converted measured value is sent to the overall control unit 15 and then reported by being outputted to the monitor of the display unit 16 or being printed by a printer as data corresponding to each measurement item.

Since the sample which is not determined to be sucked in an insufficient amount has no problem, it is transferred to the direct measurement line 12 through the route R3 in the state that it is sucked by the sample suction probe 2.

The above described processes will be briefly described with reference to the flowcharts shown in FIG. 8.

Referring to FIG. 8, when it is required to carry out the sampling process, a sampling start instruction is first made and then, in step S1, the control unit instructs to the drive unit 5 to move the probe 2 for sucking discriminated by the suction monitor 3 whether or not the predetermined amount of the sample can be sucked, and if YES, the sample vessel 1A is transferred directly to the reaction vessel 12A of the measurement line 12 and if No, that is, being discriminated that the sample amount is insufficient, the sample is delivered to the sample temporary storage unit 6.

In step S3, the sample quantity determination probe 7 is operated to determine the sample amount, that is, the top level of the sample in the vessel 6A is detected for ensuring the minimum amount of the sample sucked. This data is sent to the control unit 15 and the insufficient amount of the sample is calculated in step S4. In this step S4, the magnification ratio for dilution, in a case where the calculated insufficient amount of the sample is substituted by pure water, is also calculated. The results of these calculations are stored in the measurement control unit 14. In the next step S5, in accordance with the above calculations, the sucked insufficient amount of the sample and the added dilution solution are transferred in the reaction vessel 12A.

The samples transferred to the measurement line 12 are subjected to the concentration calculation, step S6, to determine whether or not the sample in the reaction vessel 12A is the diluted sample, and if YES, in step S7, the concentration is converted into an actual concentration value by considering the magnification ratio for dilution. The result of this calculation is displayed to the monitor or printed by the printer as data in step S8. These processes are automatically repeated.

According to the present embodiment, the sample the sucked amount of which is detected to be insufficient prior to analysis is transferred to the temporary sample storage unit 6 instead of being directly transferred to the measurement line 12. An insufficient amount of the sample is calculated and the magnification ratio for dilution for increasing the amount of the sample to an amount necessary for measuring the sample is determined in the sample temporary storage unit 6. Thereafter, the sample is transferred to the measurement line 12. The sample is measured in the same way as that of a usual sample of sufficient amount and the measured value is corrected on the basis of the magnification ratio for dilution. Therefore, even if a sample is insufficiently sucked, the sample is used as it is and subjected to analyzing process after having been diluted. Accordingly, the sample is not wasted. Further, since the sample need not be remeasured, a time consumed by the remeasurement is saved. It is also to be noted that since a method for determining the quantity of a sucked sample is not required to have a strict accuracy as compared with that required when a sample is sucked or discharged, this method can be realized within the range of usual technologies.

Further, since the process for determining a quantity of an insufficiently sucked sample by the sample quantity determination unit 7 in the temporary sample storage unit 6 is carried out concurrently with the usual process for sucking a sample from the sample vessel 1A by the sample suction probe 2, an analysis efficiency is not lowered at all.

Although the present invention is described with respect to an example in which the sample suction probe 2 is prepared independently of the sample quantity determination probe 7, a single probe acting as both the sample suction probe 2 and the sample quantity determination probe 7 may be used. Further, although a method of determining the quantity of a sample in the vessel 6A by the temporary sample storage unit 6 is described with reference to the example in which an amount of vertical movement of the sample quantity determination probe 7 is utilized, the present invention is not limited to this method, and a level height may be determined by using an optical method or a sucked amount may be set as V1 based on a change of a detection signal from the suction monitor 3 and the operation of the pump 4.

What is claimed is:

1. A chemical analysis system in which a sample and a reagent supplies in a reaction vessel disposed in a measurement line are subjected to analysis treatment and an analyzed result is then reported, comprising:

means for sucking the sample from a sample vessel;

means for detecting a fact as to whether a sucked amount of the sample is sufficient or insufficient for the analysis treatment;

means for calculating an insufficient amount of the sucked sample when it is detected by the detecting means that an insufficient amount of the sample necessary for the analysis is sucked and for obtaining an information regarding an amount of a dilution solution necessary for compensating for the insufficient amount of the sample;

means for adding said amount of said dilution solution to said insufficient amount of the sample necessary for compensating for said insufficient amount of the sample;

means for carrying out an analysis treatment of the diluted sample in accordance with the information of the amount of the dilution solution added to said insufficient amount of the sample; and means for compensating for said analyzed result of the analysis treatment in accordance with the information of the amount of the dilution solution.

2. A chemical analysis system, comprising:

a sample setting unit for accomodating a plurality of sample vessels, each containing a respective sample to be analyzed;

a suction unit for sucking the sample from one of said plurality of sample vessels and detecting whether the sucked sample is of a sufficient or insufficient amount for analysis;

a temporary sample storage unit including at least one temporary sample storage vessel for storing a sample sucked by said suction unit and detected to be of an insufficient amount for analysis;

a measurement unit, including a sample reaction vessel for receiving said insufficient amount of sample from said temporary suction unit;

a transferring means for transferring said insufficient amount of sample from said temporary storage unit to said measurement unit;

a reagent setting unit for supplying a reagent into said sample reaction vessel for mixture with said insufficient amount of sample;

a dilution unit for diluting said insufficient amount of sample mixed with said reagent in said sample reaction vessel;

control means for controlling said suction unit, said temporary sample storage unit and said dilution unit, said control means comprising means for controlling transfer of samples from said sample setting unit to said temporary sample storage unit and said control means further comprising means for calculating an amount of insufficiency of an insufficient sample and for determining information representing an amount of a dilution solution which is necessary to be added to said insufficient amount of sample in order to perform said analysis, a means for carrying out said analysis after dilution of said insufficient sample on the basis of said information representing said necessary amount of dilution solution to be added to said insufficient amount of sample, and a means for compensating for a result of said analysis based on said information representing said necessary amount of dilution solution to be added to said insufficient amount of sample; and means for displaying said result of said analysis of said insufficient amount of sample.

3. A chemical analysis system according to claim 2, wherein the suction unit includes a sample suction probe for sucking the sample from the sample vessel disposed in the sample setting unit and a suction monitor for detecting whether or not a sufficient amount of the sample has been sucked.

4. A chemical analysis system according to claim 2, wherein the temporary sample storage unit includes a sample quantity determination probe for determining an amount of the sample in the temporary sample storage vessel transferred to the temporary sample storage unit, said sample quantity determination probe being provided with a level sensor for detecting a surface level of the sample contained in the sample vessel.

5. A chemical analysis system according to claim 2, wherein the dilution solution is pure water and the sample of the insufficient amount is diluted by an amount of the pure water calculated by said control means.

6. A chemical analysis system according to claim 5, wherein the result of the analysis is converted into an actual concentration value in accordance with said amount of dilution.

7. A chemical analysis method for sucking a sample in a sample vessel and analyzing the sample in a measurement line, comprising the steps of:

sucking a sample from the sample vessel;

discriminating whether the sucked sample is of a sufficient or insufficient amount;

transferring a sample discriminated to have a sufficient amount directly to a measurement line and separately transferring a sample discriminated to have an insufficient amount;

calculating an insufficient amount of the separately transferred sample;

calculating an amount of dilution solution which is necessary to be added to the sample of the insufficient amount in order to perform analysis of the sample, said amount being calculated in accordance with the amount of insufficiency of the sample;

supplying said dilution solution to said sample of the insufficient amount in an amount in accordance with the amount of dilution solution calculated;

transferring the thus diluted sample to the measurement line;

calculating a concentration of the diluted sample transferred to the measurement line in order to determine the amount that the sample as been diluted;

calculating an actual concentration of the sample of insufficient amount transferred to the measurement line in accordance with the amount of dilution; and carrying out a chemical analysis of the sample of insufficient amount using said actual concentration of the sample of insufficient amount.

* * * * *